US005968063A

United States Patent [19]

[11] Patent Number: 5,968,063

[45] Date of Patent: Oct. 19, 1999

Chu et al.

[54] INTRAMUSCULAR STIMULATION THERAPY FACILITATING DEVICE AND METHOD

[75] Inventors: Jennifer Chu, 2 Barrister Ct., Haverford, Pa. 19041; Zhen Guo Yan, Shanghai, China

[73] Assignee: Jennifer Chu, Haverford, Pa.

[21] Appl. No.: 08/856,064

[22] Filed: May 14, 1997

[51] Int. Cl.[6] .................... A61B 17/34

[52] U.S. Cl. .................... 606/185; 606/189; 604/117

[58] Field of Search .................... 606/1, 129, 185, 606/189, 186; 604/158, 264, 272, 239, 156, 117, 159

[56] References Cited

U.S. PATENT DOCUMENTS

| | | |
|---|---|---|
| 4,180,079 | 12/1979 | Wing . |
| 4,276,879 | 7/1981 | Yiournas . |
| 4,613,328 | 9/1986 | Boyd . |
| 4,662,363 | 5/1987 | Romano et al. . |
| 4,758,227 | 7/1988 | Lancaster, Jr. et al. . |
| 5,199,952 | 4/1993 | Marshall, Sr. et al. . |
| 5,211,175 | 5/1993 | Gleason et al. . |
| 5,535,746 | 7/1996 | Hoover et al. . |
| 5,735,868 | 4/1998 | Lee .................... 606/189 |

OTHER PUBLICATIONS

Jennifer Chu, M.D., "Dry Needling (Intramuscular Stimulation) in Myofascial Pain Related to Lumbosacral Radiculopthy", 1995, Eur. J. Phys. Med. Rehabil. 1995:5 No. 4, pp. 106–120.

Jennifer Chu, M.D., Comment on the Simons Literature Review Column, 'Myofascial Pain Syndrome—Trigger Points', J. Musculoskeletal Pain, vol. 5(1) 1997, pp. 133–135.

Photographs of IMS device purchased from Mr. Young H. Lee in Feb., 1996.

C. C. Gunn, et al., "Dry Needling of Muscle Motor Points for Chronic Low–Back Pain: A Randomized Clinical Trial With Long–Term Follow–Up", Spine, vol. 5, No. 3, May/Jun. 1980, PP. 279–291.

C. Chan Gunn, M.D., "Treating Myofascial Pain: Intramuscular Stimulation (IMS) for Myofascial Pain Syndromes of Neuropathic Origin", 1989.

C. Chan Gunn, M.D., "The Gunn Approach to the Treatment of Chronic Pain: Intramuscular Stimulation for Myofascial Pain of Radiculopathic Origin", (2d ed.), 1996.

Open letter re IMS treatment offered by Jennifer Chu, M.D., University of Pennsylvania Medical Center, Mar. 13, 1996.

"Patient Information on Intramuscular Stimulation (IMS) For Management of Soft–Tissue/Neuropathic Pain", University of Pennsylvania Medical Center, Apr. 8, 1996.

Travell, J.G., Simons, D.G., "Myofascial Pain and Dysfunction: The Trigger Point Manual", vol. 1. Williams and Wilkins, Baltimore, 1983, Table of Contents, Preface, Chapter 3 "Apropos of Muscles".

Travell, J.G., Simons, D.G., "Myofascial Pain and Dysfunction: The Trigger Point Manual", vol. 2. The Lower Extremities. Williams and Wilkins, Baltimore, 1992, Table of Contents, Chapter 2 "General Issues".

*Primary Examiner*—Michael Buiz
*Assistant Examiner*—William Lewis
*Attorney, Agent, or Firm*—Banner & Witcoff, Ltd.

[57] ABSTRACT

Intramuscular stimulation (IMS) pain relief therapy is facilitated by a hand-held tool which, once positioned against a patient's skin, can be controlled to automatically advance a needle to penetrate the patient's flesh, reciprocate the needle within the patient's flesh a predetermined number of times through a predetermined stroke, and retract the needle. A tubular guide member is provided at its distal end with a skin contact member forming a constricted orifice closely matching the diameter of the needle. The orifice allows substantially free passage of the needle therethrough and at the same time prevents bowing of the needle as it is advanced—a primary source of patient pain. Automation and control of the needle penetration, reciprocation and retraction sequence reduces the amount of manual and mental effort required on the part of the treating physician, thereby allowing physicians to perform IMS procedures more consistently, effectively and efficiently. This leads to better results (increased pain relief), decreased procedure induced patient pain and tissue trauma, and reduced risk of repetitive strain injury to the treating physician.

22 Claims, 6 Drawing Sheets

INTRAMUSCULAR STIMULATION THERAPY FACILITATING DEVICE AND METHOD

BACKGROUND OF THE INVENTION

The present invention relates to pain management. In particular, the invention relates to intramuscular stimulation therapy utilizing pin (i.e. needle) penetration and manipulation to help relieve severe chronic pain for which a specific cause cannot be determined, and for which medicinal and other usual methods of pain relief have proven ineffective, i.e., neuropathic pain.

Non-chemical, non-electrical intramuscular stimulation (IMS) is used in the management of regional and diffuse myofascial pain (fibromylagia) of radiculopathic origin where musculoskeletal pain resulting from muscle shortening is the predominant feature. Unlike acupuncture, where many pins which remain stationary are inserted into points on imaginary meridians, in IMS generally only one pin is used at a time. The pin, which is inserted into a tender muscle motor point, is continuously manipulated to achieve pain relief. The IMS technique was pioneered by C. Chan Gunn, M.D. and is described in the following publications, each of which is, in its entirety, incorporated by reference herein: Gunn C. C. et al., Dry Needling of Muscle Motor Points for Chronic Low-Back Pain, A Randomized Clinical Trial With Long-Term Follow-Up, *Spine*, Vol. 5 No. 3, May/June 1980, pp. 279–291; Gunn C. C., Treatment of Chronic Pain. Intramuscular Stimulation for Myofascial Pain of Radiculopathic Origin. London, UK, Churchill Livingston, 1996.

Building on the work of Gunn, and based upon a clinical study of pain relief experienced by patients who have undergone electromyography (EMG) to determine the effects of IMS on pain symptoms, the present physician inventor developed and has used with success a modified IMS technique. In EMG, a pin electrode is inserted into muscles for detection of electromyographic signals. During EMG, the pin is moved in all directions for examination of the electrical activity of the muscle during rest, and minimal and maximal contraction. The inventor's modified IMS technique focuses on eliciting twitch responses from muscles by stimulation of motor end plate zones, as opposed to stimulation of motor points as described by Gunn. In the inventor's original technique, a somewhat randomly directed needle insertion was followed with needle movement in all directions and at different depths in the muscle, as in EMG studies, in order to localize and accurately position the pin in the motor end-plate zone. See Chu J., Dry Needling (Intramuscular Stimulation) In Myofacsial Pain Related To Lumbosacral Radiculopathy, *Eur. J. Phys. Med And Rehabil.* 5(4): 106–121, 1995 (hereby incorporated by reference in its entirety). Later, the present inventor observed that increased pain relief effects could be obtained by needling muscle tender points with a simple in-out motion of a needle along the myofascial bands of the muscles.

IMS, whether in accordance with the modality taught by Gunn or that taught by the present inventor, has been performed manually. In accordance with Gunn's teaching, a thin flexible acupuncture needle is inserted into the patient's flesh utilizing a tubular guide. The needle is attached at its proximal end to a distal end of a plunger which is reciprocable within the guide. The plunger protrudes from the proximal end of the tubular guide to provide a finger grip surface, whereby the plunger (and attached needle) can be advanced and retracted. An example of such a tubular guide is the Showa #6 available from Nikka Industries Ltd., Vancouver, B.C., Canada. In accordance with the inventor's modified IMS technique, the same type of tubular guide can be used. However, a stiffer EMG needle is preferred for certain applications.

Despite its effectiveness in ultimately providing pain relief, the manual IMS treatment is itself quite painful to the patient. The pain is primarily due to the irregular deflection of the needle from its proper path as it is manually pushed in and pulled out repetitively through tissues of differing resiliencies. With the manual method of IMS, it is difficult to maintain proper positioning and directivity of the needle insertion with each to and fro movement, because of the manual effort required of the physician. As a result, the twitch point is easily lost. In such a situation, the pin direction is changed (often several times) within the muscle in order to return the pin to the vicinity of the twitch point. This causes significant additional discomfort to the patient, as well as increased bleeding and tissue trauma. Uneven starts and stops within the muscle are also inevitable because the movements are dependent on the treating physician's skill and strength on encountering different resistance of skin, subcutaneous and muscle tissue at any given point. Less pain would be experienced by the patient if the pin movements could be kept regular, even and steady.

In addition, the work involved on the physician's part in performing manual IMS is laborious, tedious, time-consuming and likely to lead to repetitive stress injury. This is due to the repetitive and resisted upper extremity movements required in performing the procedure. The problem for physicians is particularly acute when, as is typically the case, many areas of a patient's body have to be treated in one session, and when the majority of the patients require this type of multi-area treatment. Under these circumstances, physicians performing manual IMS on a long term basis likely will suffer from repetitive strain injuries and eventually have to stop practicing the method.

SUMMARY OF THE INVENTION

In view of the foregoing, it is an object of the present invention to reduce tissue trauma and patient discomfort associated with IMS procedures.

It is a further object of the invention to facilitate physicians'performance of IMS procedures by providing controllable automation of IMS pin insertion and retraction movements, whereby better and more consistent results may be obtained, with less effort and risk of repetitive stress injury on the part of the physician.

These and other objects are achieved in accordance with the present invention by an automatic needling device for facilitating intramuscular stimulation pain relief therapy. The device includes an elongated guide tube having a skin contact member at its distal end. A plunger is reciprocable within the guide tube. The plunger has a proximal end protruding from a proximal end of the guide tube and a distal end retained within the tube and providing a needle holder. A needle is securable at its proximal end to the needle holder and is reciprocable with the plunger for movement into and out of the guide tube through the skin contact member. A motorized mechanism is attached to the protruding proximal end of the plunger for reciprocating the plunger within the guide tube. This causes a needle secured to the needle holder to reciprocate in and out of said guide tube through the skin contact member. Electronic circuitry is provided for controlling the motorized mechanism to advance the needle out of the guide tube to a predetermined penetration depth, reciprocate the needle back and forth through a predetermined stroke length a predetermined number of times, and retract the needle into the guide tube.

In a second aspect, the invention is embodied in an automatic needling method for facilitating intramuscular stimulation pain relief therapy. An automatic needling device is pre-positioned for needle penetration at a chosen site on a patient's skin. The automatic needling device is controlled to automatically advance a needle thereof to a predetermined penetration depth within the patient's flesh, reciprocate the needle back and forth through a predetermined stroke length a predetermined number of times, and retract the needle from the patient's flesh, while maintaining the needling device at the chosen site.

In a third aspect, the invention is embodied in a needling device for facilitating intramuscular stimulation pain relief therapy. The device includes an elongated guide tube having a skin contact member forming a constricted opening at a distal end of the tube. A plunger is reciprocable within the guide tube. The plunger has a proximal end protruding from a proximal end of the guide tube and a distal end retained within the tube and providing a needle holder. A needle is securable at its proximal end to the needle holder and reciprocable with the plunger for movement into and out of the guide tube through the constricted opening of the skin contact member. The constricted opening is sized large enough to allow substantially free passage of the needle back and forth therein but small enough to serve as a needle guide preventing significant flexing of the needle at the point of entry into a skin surface contacted by the skin contact member.

The above and other objects, features and advantages of the present invention will be readily apparent and fully understood from the following detailed description of preferred embodiments, taken in connection with the appended drawings.

DETAILED DESCRIPTION OF THE PREFERRED EMBODIMENTS

Figure 1:
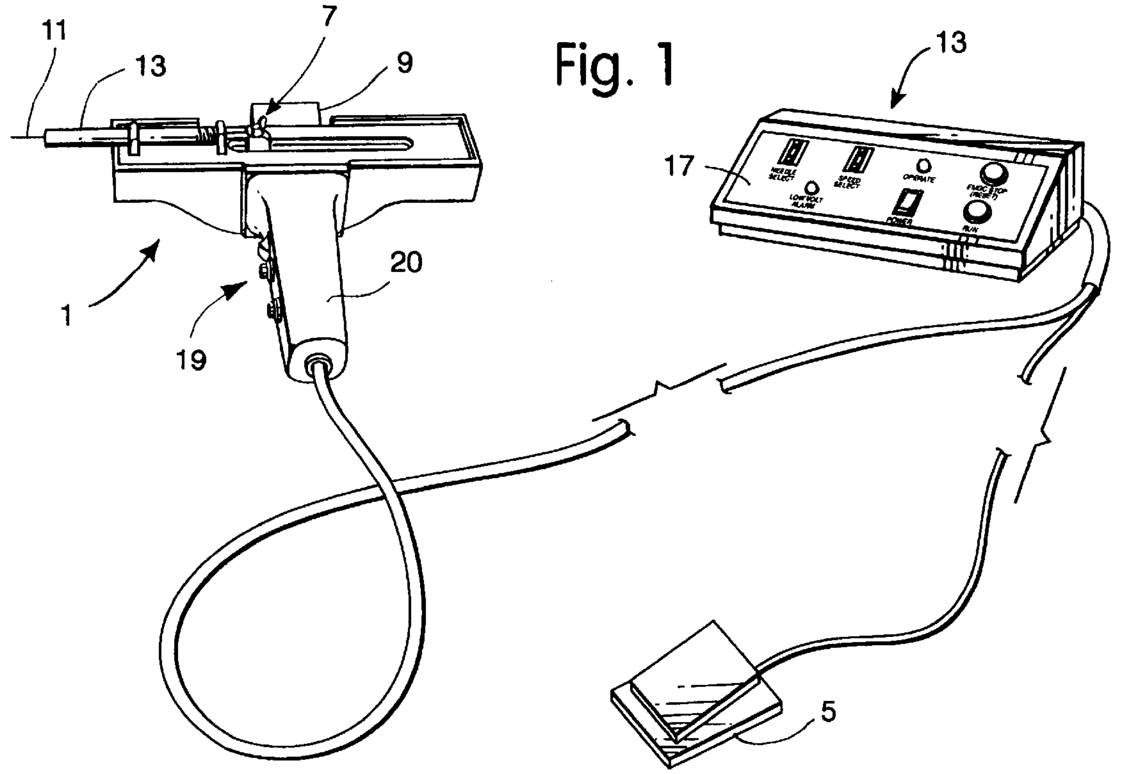
FIG. 1 is an overall perspective view of an automated intramuscular stimulation system in accordance with the present invention.
Figure 7:
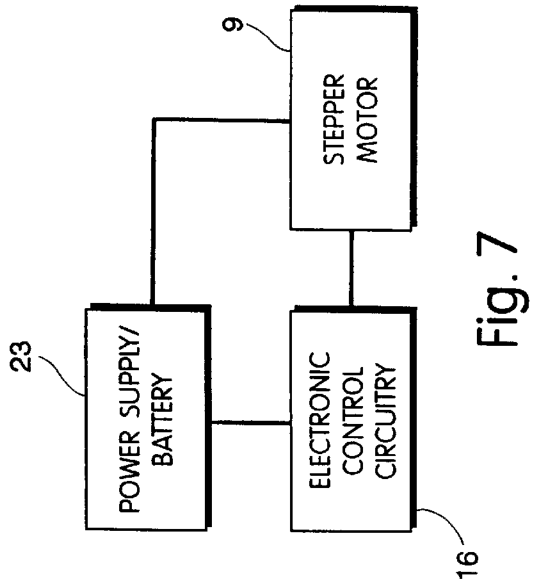
FIG. 7 is a block diagram depicting the electrical components of the system illustrated in FIG. 1.

As shown in FIG. 1, an automated intramuscular stimulation system in accordance with the present invention includes a hand-held needling tool 1, an electronic control box 3 and a footswitch 5. Needling tool 1 comprises a needle shuttle mechanism 7 driven by a motor 9 for reciprocating a needle 11 in and out of an elongated guide tube 13, through a skin contact member 15 (see FIG. 4) provided at a distal end of tube 13. Electronic circuitry 16 (see FIG. 7) contained within control box 3 is controllable by user accessible switches to control motor 9 in a predetermined manner (to be described). The switches are provided on a control panel 17 of control box 3, as footswitch 5 and as switches 19 on a hand grip 20 of tool 1.

Figure 3:
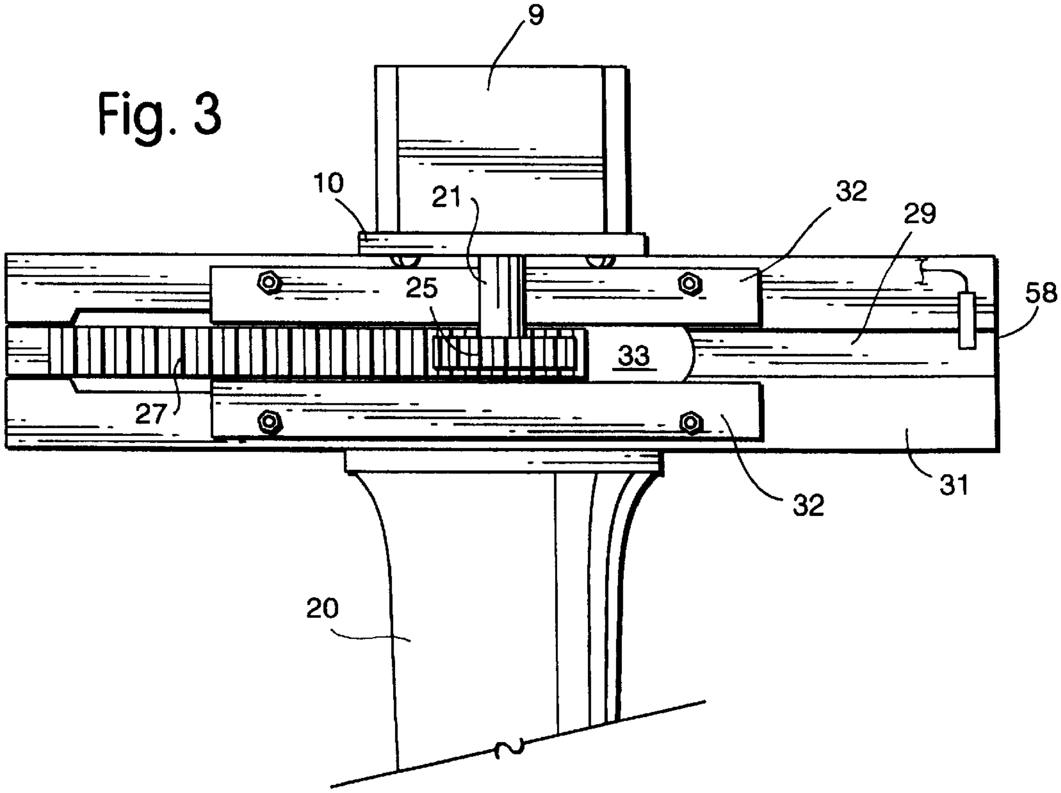
FIG. 3 is a partial right side elevation view of the tool shown in FIG. 2, with a cover piece removed to reveal internal components.
Figure 4:
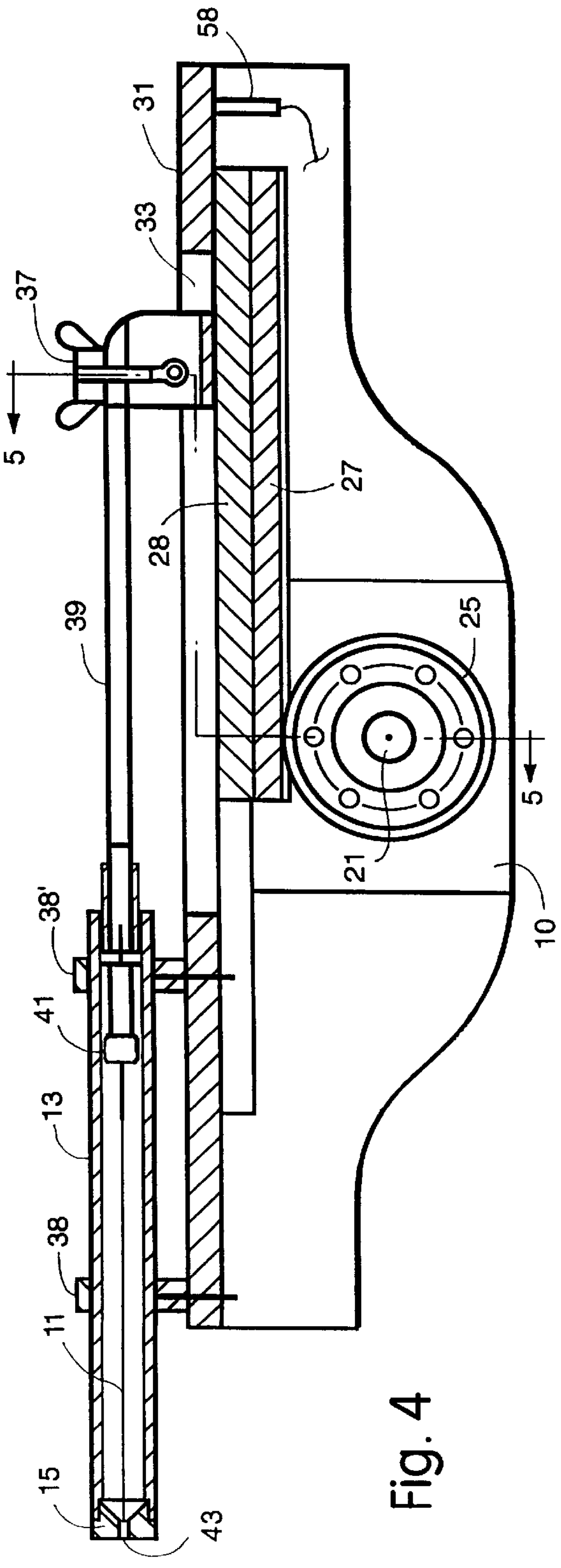
FIG. 4 is a cross-sectional view taken on line 4—4 of FIG. 2.
Figure 5:
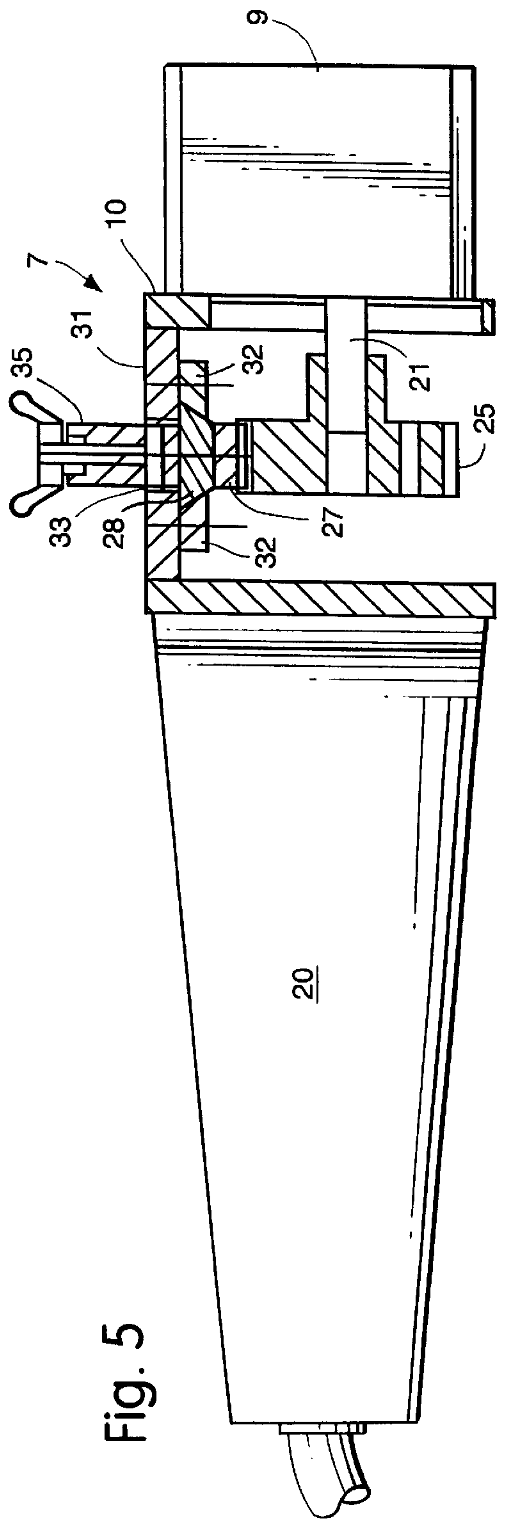
FIG. 5 is a cross-sectional view taken on line 5—5 in FIG. 4.

In the illustrated preferred embodiment, motor 9 is a stepper motor attached to a rigid chassis plate 10 (see FIGS. 3–5). Motor 9 has a rotatable shaft 21 which is rotated (clockwise and counterclockwise) in very small increments under the control of digital pulse trains received from conventional stepper motor driver circuitry included in circuitry 16. In a manner to be explained, the rotary motion of motor shaft 21 is translated into reciprocating movement of needle 11. Circuitry 16 is a digital logic circuit constructed in accordance with known techniques (e.g., as an application specific integrated circuit (ASIC), hardwired printed circuit board mounted components, or a suitably programmed general purpose chip/computer) to achieve a novel motor (and hence needle movement) control functionality, as will be described. The control is carried out in accordance with actuation and settings of the user operable switches. As depicted by box 23 in FIG. 7, D.C. electrical power for control circuitry 16 and motor 9 may be supplied by one or more batteries contained within (or outside of) control box 3, or by a suitable power supply serving to convert AC line voltage to DC.

It will be appreciated that with a miniaturization of the circuitry components possible within the state of the art, control circuitry 16 can be incorporated into needling tool 1, thereby eliminating the need for a separate control box. Conversely, it is desirable to completely omit control switches from tool 1 in order to reduce the size and weight of the tool and to avoid the possibility of inadvertent switch actuation during performance of IMS procedures.

As best seen in FIGS. 3–5, needle shuttle mechanism 7 comprises a gear wheel 25 mounted for rotation with motor shaft 21. Gear wheel 25 is engaged with a flat gear 27 fixedly mounted on a carrier bar 28 (see FIGS. 4 and 5), which in turn is mounted for sliding movement within a channel 29 provided in a chassis base plate 31. Flat gear 27 is preferably formed of nylon or another known tough plastic. This reduces the weight and operational noise of the tool, as compared with a metal-to-metal gear interface. Carrier bar 28 is formed as an elongated truncated triangular prism. Bar 28 is slidably retained on base plate 31 by a pair of flat bars 32 secured to base plate 31 in a spaced parallel relationship. Flat bars 32 provide opposing tapered sidewalls which slidably capture carrier bar 28 by contact with correspondingly tapered sidewalls of bar 28. Base plate 31 also defines an elongated through-slot 33 which accommodates end-to-end reciprocable movement of a shuttle block 35 attached on a side of carrier plate 28 opposite flat gear 27.

Shuttle block 35 comprises a wing-nut clamp 37 serving to releasably capture the proximal end of a plunger rod 39 reciprocable within guide tube 13. With plunger rod 39 so captured, a distal end of rod 39 is retained within guide tube 13. The distal end is provided with a needle holder 41 of conventional design, e.g., a threaded collar clamp of the type used in the Nikka Industries tubular guide mentioned in the Background section. With a proximal end of needle 11 secured in needle holder 41, needle 11 is reciprocable into and out of guide tube 13 through skin contact member 15.

Guide tube 13 is removably secured to base plate 31 by a pair of eyelet flanges 38, 38'. Guide tube 13 is sized to slidably pass through distal eyelet 38. A proximal end of guide tube 13 has a male thread for engagement with a female thread formed in the eyelet of flange 38'. The sub-assembly of guide tube 13, skin contact member 15 and plunger rod 39 are removable as a unit (then disassemblable) for sterilization by autoclave. Each of the components is preferably made of sterilizable medical grade materials. Metals such as copper, brass and stainless steel can be used.

It will be understood that various other motorized shuttle mechanisms can be used to reciprocate needle 11. Instead of a stepper motor, an analog synchronous motor could be used together with appropriate analog control circuitry. The shuttle mechanism need not include a rotary motor and mechanical linkage for converting rotary motion to reciprocable linear motion. Instead, a motor in the form of a linear pneumatic or hydraulic actuator could be used, thereby eliminating the need for motion converting means.

Skin contact member 15 comprises a plug-like element which may be threadably or otherwise secured to the distal end of guide tube 13. Contact member 15 forms a constricted orifice sized large enough to allow substantially free passage of needle 11 but small enough to serve as a needle guide preventing significant flexing of the needle at the point of entry into a skin surface contacted by contact member 15. Needle flex at the point of entry to the skin is a primary cause of patient discomfort. By substantially eliminating such flex the constricted opening of the present invention significantly reduces patient pain associated with IMS treatments. Preferably, the constricted opening has an inner diameter which exceeds the diameter of the needle by less than 0.50 mm, so that lateral displacement of the needle at the point of skin entry is limited to this amount.

In accordance with the invention, it is preferable to use as needle 11 disposable acupuncture pins (e.g., ITO brand, Tokyo, Japan). Such pins are available in lengths ranging from 30 to 50 mm. The appropriate length is chosen according to the thickness of the skin and subcutaneous tissue overlying the muscle to be treated. For treating most muscles, a 30 or 40 mm length is generally appropriate; a 50 mm length is generally preferred for treating the gluteus maximus muscle. Such pins are typically 30 gauge (0.26 mm diameter). In cases where particularly tough skin and muscle tissue are encountered, it will be preferable to use stiffer monopolar EMG pins (e.g., TECA Corp., Pleasantville, N.Y.). Such pins are 26 gauge (0.46 mm needle diameter) and are available in lengths of 37 mm, 50 mm and 75 mm. In order to accommodate different needle diameters in the range of 0.26 to 0.46 mm, while maintaining a differential diameter of the needle and constricted opening of less than 0.50 mm, the constricted opening may be provided with an inner diameter of 0.75 mm.

Preferably, the pin (whether of acupuncture or EMG size/style) is coated with Teflon™ or a like friction reducing layer to reduce patient tissue trauma and pain upon needle insertion. Ideally, a set of needles will be provided with a range of needle diameters and lengths, but with each needle having an identical base configuration allowing ready needle interchangeability, without modification of needling tool 1. In addition, cost savings may be realized over the use of standard EMG pins by providing a simplified base structure grippable by conventional needle holder 41.

In order to smoothly guide needle 11 into constricted opening 43, skin contact member 15 is configured to taper the internal diameter of guide tube 11 up to constricted orifice 43 in a funnel-like manner. The inventors have found that a taper angle of 21° (measured between the internal funnel surfaces and surrounding walls of tubular guide 13) works well for this purpose.

Figure 8:
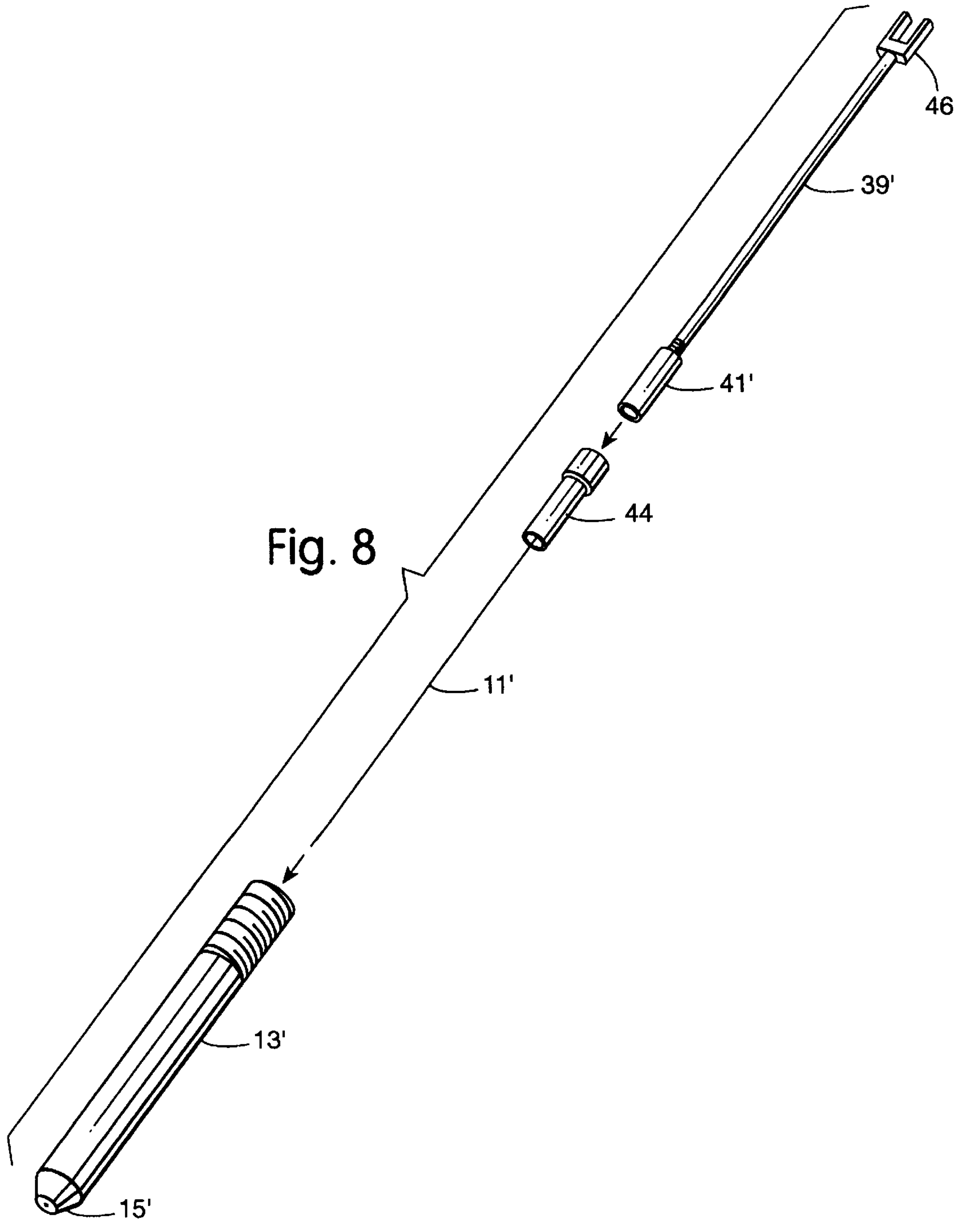
FIG. 8 is an exploded perspective view illustrating a modified embodiment of the inventive needling tool, for use with EMG needles.
Figure 9:
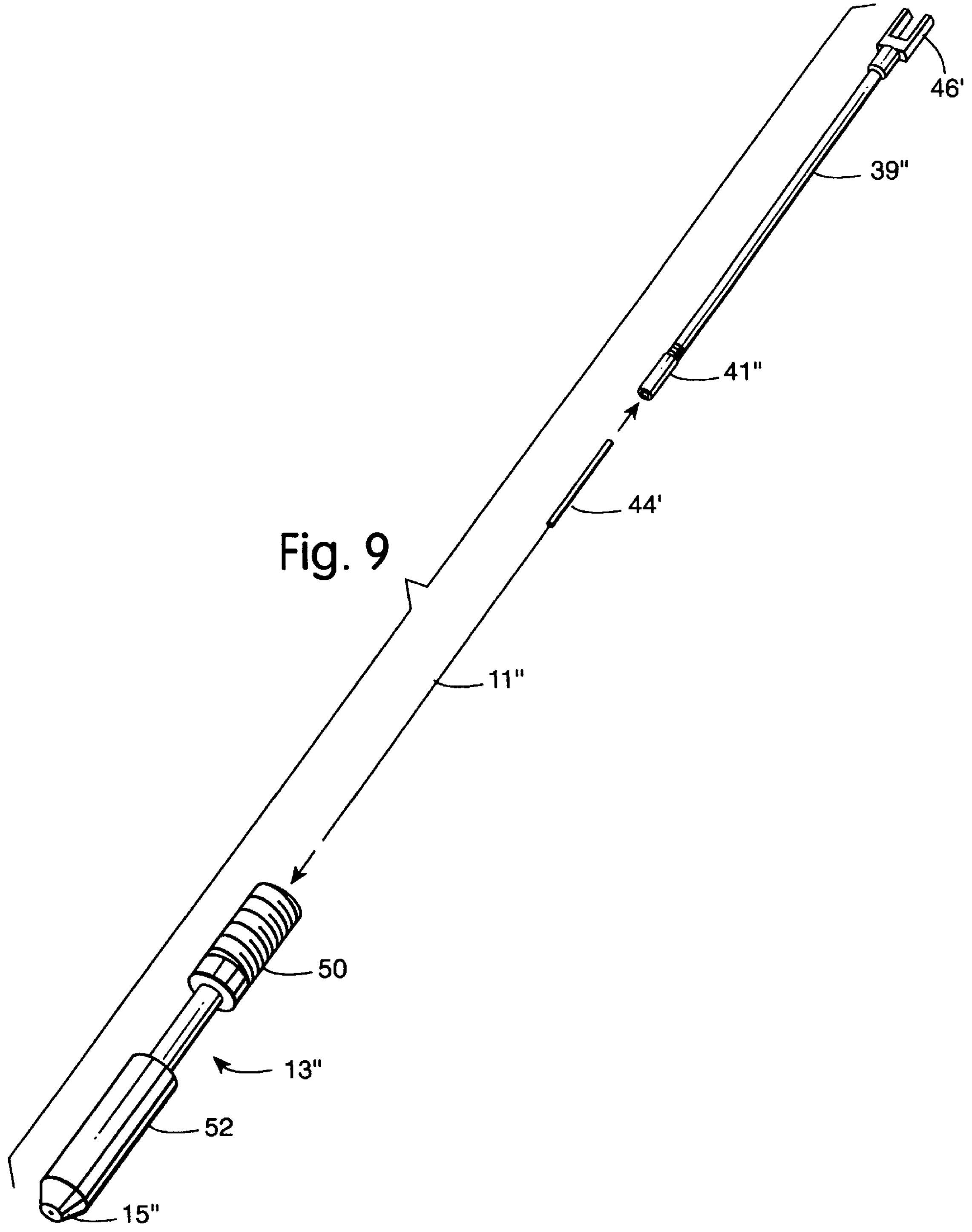
FIG. 9 is an exploded perspective view illustrating another modified embodiment of the inventive needling tool, for use with acupuncture needles.

Refined sub-assemblies of the invention are illustrated in FIGS. 8 and 9. Specifically, FIG. 8 illustrates a guide tube 13' and plunger rod 39' specially adapted for accommodating the relatively large base 44 of a standard EMG pin 11'. A yoke 46 is provided at the proximal end of rod 39' for easy removal from, and attachment in, wing-nut clamp 37. Needle holder 41' is adapted to be inserted into base 44 and to grip a cylindrical core piece therein. Tubular guide 13' has a threaded proximal end for engagement with proximal eyelet flange 38'. A skin contact member 15' is provided with a truncated frusto-conical shape in order to allow more precise positioning of the tool for needle penetration.

FIG. 9 illustrates a guide tube assembly 13" and plunger rod 39" specially adapted for accommodating the smaller base 44' of a standard acupuncture needle 11". Rod 39" has an attachment yoke 46' at its proximal end, as in the FIG. 8 embodiment. A needle holder 41" at the distal end of rod 39" releasably grips the outside of needle base 44'.

Guide tube assembly 13" comprises a small diameter tube 48 having an internal bore sized to correspond to the smaller diameter of needle holder 41". Advantageously, the smaller internal bore serves as a closer guide for the (more flexible) acupuncture needles, to thereby prevent excessive needle flex. Interchangeability with the FIG. 8 embodiment is allowed by the provision of a proximal pipe segment 50 threaded for engagement with proximal eyelet flange 38'and a distal pipe segment 52 sized for receipt in distal eyelet flange 38. Like the FIG. 8 embodiment, pipe segment 52 provides a skin contact member 15" having a truncated frusto-conical shape.

Figure 6:
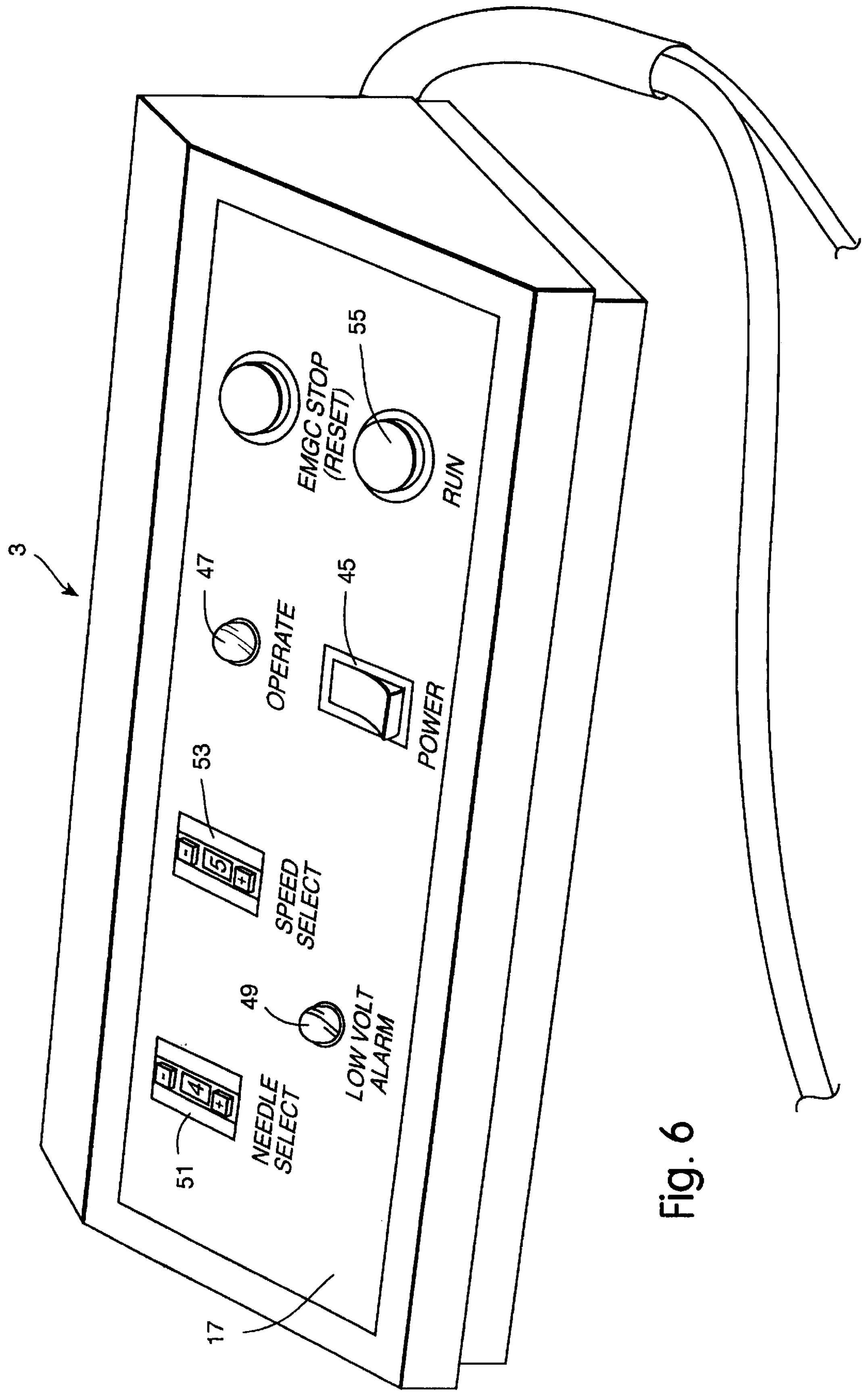
FIG. 6 is a close-up perspective view of the control box illustrated in FIG. 1.

The preferred motor control is now described. Referring to FIG. 6, control panel 17 includes a main power switch 45. An Operate light 47 provides a clear indication of whether the power is switched on or off A Low Volt Alarm light 49 indicates a condition wherein the voltage supplied by power supply/battery 23 has dropped below the required level. A needle select switch 51 is used to preset the initial penetration depth and stroke length of the needle reciprocation, based upon the length of needle 11. As shown, switch 51 can be of a conventional electronic increment/decrement type including a numeric display indicating the chosen preset. A similar type of switch 53 is used to preset the speed at which the needle will reciprocate. A Run button 55 is depressed to initiate a motor control sequence, based, in part, upon the presets of the Needle and Speed Select switches 51, 53.

If necessary, the preset motor control sequence can be interrupted by pressing an Emergency (EMGC) Stop (Reset) button 56. This will cause the needle to be immediately returned to its fully retracted position. In order to positively sense the fully retracted position, a proximity switch 58 and associated sensing circuit (not shown) are provided. Switch 58 may be a mechanical switch arranged to be closed by contact with flat gear 27 and/or carrier bar 28 when those elements reach the proximal end of their stroke. Alternatively, switch 58 can be a known photo-optical detector which senses the breaking of a light beam by flat gear 27 and/or carrier bar 28.

Figure 2:
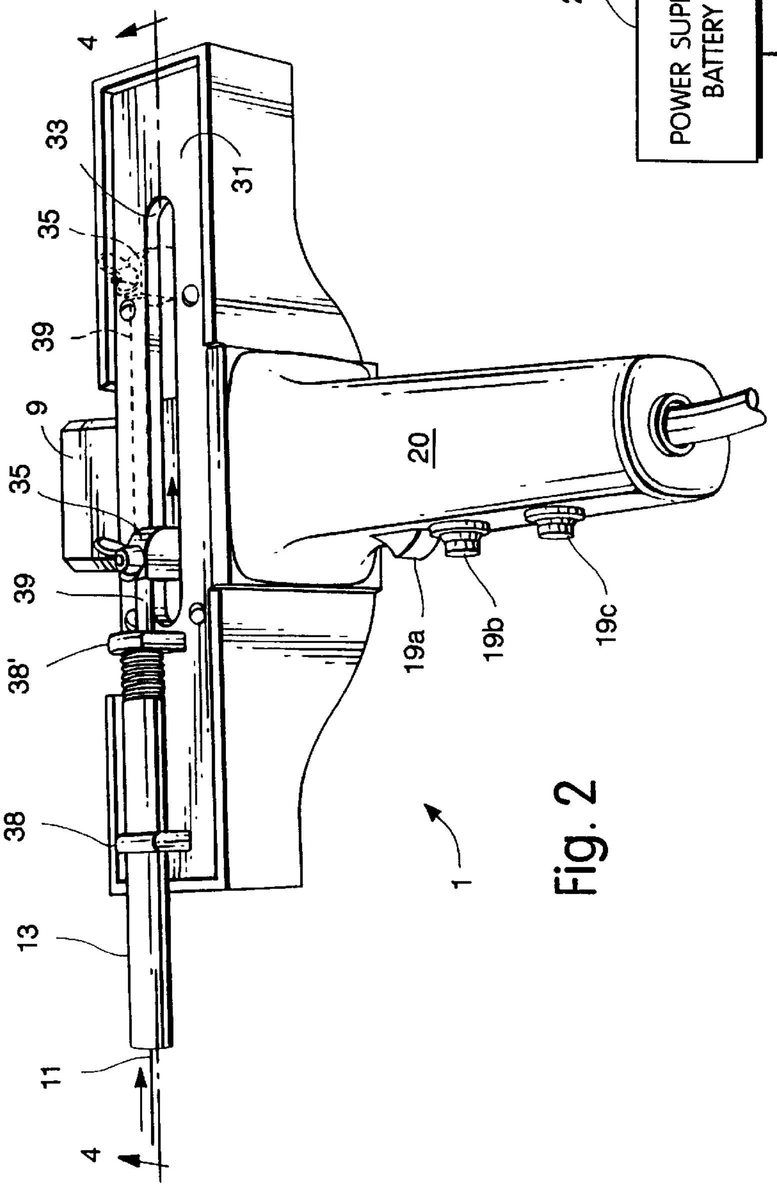
FIG. 2 is a left side perspective view of the hand-held needle reciprocating tool shown in FIG. 1, depicting both extended and retracted positions of a needle shuttle mechanism.

Footswitch 5 operates, like Run button 55, to initiate a motor control sequence, but with hands-free convenience. Redundant Power, Run and Stop switches 19*a*, 19*b*, 19*c* (see FIG. 2) may be provided on handle 20 of needling tool 1.

Upon depression of run button 55, needle 11 quickly penetrates the skin and advances to the preset penetration depth. After the preset pin depth is reached, the pin will oscillate backward and forward through a preset stroke, e.g., 20 mm, a predetermined number of times, e.g., three, at a speed determined by the Speed Select switch.

The speed at which the needle initially penetrates the skin is preferably 0.6 m/sec. The speeds at which the needle reciprocates may correspond to the preset numbers of Speed Select switch 53, as follows:

| Preset No. | Speed (cycles per second) |
|---|---|
| 1 | 1.0 |
| 2 | 1.25 |
| 3 | 1.5 |
| 4 | 1.75 |
| 5 | 2.0 |
| 6 | 2.25 |
| 7 | 2.5 |
| 8 | 2.75 |
| 9 | 3.0 |

Generally it is thought to be preferable to reciprocate the needle at a rate of between one and three cycles per second. The speed most preferred for IMS procedures is 2.0 cycles per second (Preset No. 5). The preferred predetermined number of needle reciprocations before automatic withdrawal is three. The reason for this is explained below.

The twitch point is a tender point on a thickened region of the muscle known as the myofascial band. In the preferred IMS modality, this point is localized and needling device 1 is pre-positioned on the skin over the twitch point. It has been found that a twitch from the muscle will be easily elicited within three strokes of the needle if the placement of tool 1 (and hence the needle placement) is accurate. In the event that tool 1 is misplaced or misdirected, there will be no twitches and further movements of the needle (at the same position and in the same direction) will do no good. On the other hand, if the twitch force obtained is significant and there are twitches with every pin movement, the start button can be pressed again and more twitches can be evoked by maintaining the same traectory of the pin. Since only three twitches can be evoked with every motor control sequence, the patient will have time to indicate, at short intervals, whether he/she is comfortable enough to continue with the twitching. In order to avoid excessive tissue trauma, it is believed that the number of successive treatment intervals at a given muscle point should be limited to three.

As is generally the case with invasive medical procedures, extensive specialized training and in-depth knowledge on the part of the treating physician is essential in order to achieve beneficial results (and to avoid serious injury to the patient). The following procedural guidelines will enable a physician skilled in IMS therapy to practice the present physician inventor's preferred modality of IMS. That modality focuses on the automated elicitation of twitch responses, i.e., automated twitch obtaining intramuscular stimulation (ATOIMS™).

GENERAL PRINCIPLES

1. A sound knowledge of anatomy is essential. The trainee is referred to Gray's Textbook of Anatomy, Lea & Febiger, Philadelphia, 1995 and to the physician inventor's textbook, Chu-Andrews J: Electrodiagnosis: An Anatomical and Clinical Approach, JB. Lippincott, Philadelphia, 1986.
2. The muscle must always be grasped between the treating physician's thumb and the fingers. The direction of the pin must be from the thumb towards the fingers. This will avoid accidental puncture of an internal organ or intramuscular nerves and blood vessels. The thumb must be placed on the myofascial band to be treated and the guide tube 13 is placed close to the thumb.
3. If twitches are not obtained by the second site for skin penetration of the muscle in a given position, do not pursue treating the muscle in this position to avoid any further unnecessary trauma Position the muscle or the patient differently and re-instate the treatment. The best twitches are obtained when the needle axis is transverse to the direction of the muscle fibers.
4. The chosen point for treatment should not be treated for more than 3 repetitions of the 3-cycle movement of the pin.
5. The axis of the needle must be horizontal to the axis of the bone and directed away from the bone. Vertical penetration towards the bone should be avoided, except in the treatment of the paraspinal muscles.
6. When bone is accidentally touched, the facilitator must immediately be withdrawn so that the pin is retracted out of the muscle. The pin must be changed to a shorter length.
7. Avoid treatments close to surface veins in order to avoid hematomas. The facilitator must not be used for muscles which overlie internal viscera, e.g., the rhomboids major and minor muscles, the levator scapulae, the serratus anterior muscles which overlie the lungs, or the abdominal muscles which overlie the abdominal organs.
8. 40–50 mm pins are generally adequate to treat most muscles. If the patient is thin, 30–40 mm pins should be used. Generally, start the treatment with the acupuncture pin; only when this is not feasible because of skin/tissue toughness, should an EMG pin be used. In the hand or foot, acupuncture pins should be used. Thick muscles such as the gluteus maximus may need 50–75 mm length pins. Teflon™ coated pins are preferable to reduce trauma to tissues and patient pain upon pin insertion.
9. Always keep the patient close to the treating physician; avoid having to stretch or lean over the patient, which may tire and injure the physician's muscles unnecessarily. The elbows of the treating physician should be kept close to the body and the wrist close to the neutral position.
10. The treating physician should take precautions against self-injury with the treating pin while treating the patient. Gloves and other protective attire should always be worn.
11. Treatment sessions should not last longer than 20–30 minutes. Appointments should be spaced with time for rest to avoid repetitive strain injuries to the treating physician.

PATIENT CONTRA-INDICATIONS—EXCLUSION FROM THE ATOIMS™ METHOD OF TREATMENT

Patients excluded are those with diseases in which pain is not of neuropathic origin or is too advanced and, therefore, refractory to ATOIMS™ method or those patients in whom ATOIMS™ would be contraindicated. These include those patients with:

1. previous multiple spinal surgeries with or without instrumentations;
2. opiate narcotics for control of pain;
3. significant disc herniations with spinal nerve root or spinal cord compressions;
4. significant spinal stenosis or spinal instability;
5. pain related to nociception, such as surgically or traumatically induced wounds or fractures;
6. pain related to metabolic or endocrine diseases;

7. pain related to auto-immune diseases;
8. pain related to malignancy;
9. pain secondary to psychiatric causes;
10. blood dyscrasias, or those who are on medications that reduce the coagulability of blood, or who are on immunosuppressive medications;
11. skin infections and skin diseases;
12. implants, pacemakers, or pregnancy;
13. inflammatory joint disease;
14. morbid obesity;
15. advanced peripheral neuropathies, or central nervous system diseases; and/or
16. inability to follow instructions or make decisions independently.

POSITIONING UPPER EXTREMITY MUSCLES FOR THE ATOIMS™ TREATMENT

Note: It is always important to grasp muscle tissue and identify the myofascial band before needling tool 1 is started.

I. TRAPEZIUS

A. The suggested pin length is 37 mm or 50 mm according to the thickness of the tissue.

B. Supine

1. In this position, the treating physician stands at the head of the table.
2. Upper trapezius can be treated by holding the anterior border of the trapezius between the thumb, placed anteriorly, and the other fingers placed posteriorly.
3. Guide tube 13 of needling tool 1 is positioned by the thumb so the axis of the pin is perpendicular to the treatment table and the direction of the pin is toward the other fingers.

C. Prone

1. In this position, the treating physician stands at the head of the table.
2. The patient lies face-down with the arm overhead and slightly abducted.
3. The site at the upper border of the trapezius is held between the thumb placed dorsally, and the other fingers placed ventrally.
4. Guide tube 13 is positioned so the axis of the pin is perpendicular to the treatment table and the direction of the pin is toward the other fingers.

D. Side Position

1. In this position, the treating physician either sits or stands behind the patient.
2. The patient lies on the side to be treated e.g., the left side is on the lower side for optimal treatment of the left trapezium. The left arm is kept forward at 90° to the trunk and the left elbow is bent 90° to the arm in the position for external rotation of the left shoulder (Statue of Liberty holding the torch).
3. The left trapezius is treated by holding the upper edge of the left trapezius between the thumb placed dorsally and the other fingers placed ventrally.
4. Guide tube 13 is positioned by the thumb so the axis of the pin is parallel to the plane of the treatment table and the direction of the pin is towards the other fingers.
5. The opposite right shoulder can be treated from the same position.
   a. The right shoulder is placed in internal rotation with the right arm at 90° to the trunk and the elbow bent to 90° with the palm of the hand placed flat on the treatment table. The hand is placed at about mid-chest level on the treatment table.
   b. The right trapezius is grasped between the thumb, placed dorsally and the other fingers, placed ventrally.
   C. Guide tube 13 is positioned so the pin axis is parallel to the plane of the treatment table and the direction of the pin is towards the other fingers.

II. SUPRASPINATUS

A. A 25 mm length pin is suggested for treating this muscle.

B. Side Position

1. In this position, the treating physician is at the head of the table.
2. The patient is positioned lying on the side opposite that to be treated, e.g., side-lying on the left with the right shoulder of the side to be treated uppermost. The right arm is abducted to 90' and elbow bent to 90'as in internal rotation to treat the right side. The hand is placed at about mid-chest level with palm down on the examination table.
3. The treating physician feels for a point one inch medial to the junction of the lateral angle of the spinous process of the scapula and clavicle.
4. Guide tube 13 is positioned at the above point and is pointed towards the foot of the table with the axis of the pin kept parallel to the surface of the treatment table.

III. TERES MAJOR

A. A 37 or 50 mm pin is suggested for treating this muscle.

B. Side Position

1. In this position, the treating physician is at the side of the table, standing behind the patient.
2. The patient is positioned as for treating the supraspinatus muscle (see B2 above).
3. A point which is one inch proximal to the inferior lateral border of the scapula is palpated. The thumb is placed on the dorsal aspect at the above point close to this border and the fingers are placed ventrally to grasp the muscle.
4. Guide tube 13 is positioned close to the thumb so the axis of the pin is parallel to the plane of the table and the direction of the pin is toward the other fingers.

IV. LATISSIMUS DORSI

A. A 37 or 50 mm pin is suggested for treating this muscle.

B. Side Position

1. In this position, the treating physician is at the side of the table, standing behind the patient.
2. The patient is positioned lying on the side opposite that which is to be treated.
3. The lateral edge of the muscle is grasped between the thumb, placed dorsally, and the other fingers, placed ventrally. The muscle is pulled away from the chest wall.
4. Guide tube 13 is positioned close to the thumb so the axis of the pin is parallel to the plane of the table and the direction of the pin is toward the other fingers.

C. Prone

1. In this position, the treating physician is at the side of the table on the side to be treated.
2. The lateral edge of the muscle is grasped laterally between the thumb, placed dorsally, and the other fingers, placed ventrally.
3. Guide tube 13 is positioned so the axis of the pin is perpendicular to the plane of the table. The needle pipe is positioned close to the thumb and the direction of the pin is towards the other fingers.

D. Supine

1. In this position, the treating physician is at the side of the table on the side to be treated.
2. The lateral edge of the muscle is grasped laterally between the thumb, placed ventrally, and the other fingers, placed dorsally.
3. Guide tube 13 is positioned so the axis of the pin is perpendicular to the plane of the table. The needle pipe is positioned close to the thumb and the direction of the pin is towards the other fingers.

V. DELTOID

A. A 50 mm pin is suggested for treating this muscle.

B. The physician is positioned at the side of the table on the side to be treated.

C. Supine

1. The patient' s arm is positioned 90° to the trunk and the elbow is bent 90° for the anterior and middle deltoid (Statue of Liberty holding the torch) position.
2. The anterior deltoid is grasped between the fingers with the thumb on the ventral aspect and the other fingers on the dorsal aspect. Guide tube 13 is positioned close to the thumb so the axis of the pin is parallel to the plane of the table. The direction of the pin is towards the other fingers.
3. The middle deltoid can be treated by pulling the muscle fibers between the fingers and positioning guide tube 13 so the axis of the pin is perpendicular to the plane of the table. The pin is positioned close to the thumb and is directed towards the other fingers.
4. The arm is placed overhead with the elbow bent to treat the posterior deltoid. Guide tube 13 is positioned parallel to the plane of the bed and the pin is pointed in a distal-to-proximal direction.

D. Prone

1. The treating physician stands at the head of the table.
2. The patient's arm is positioned overhead and the arm is slightly abducted.
3. The lower part of the posterior deltoid muscle is treated at 1–2 inches lateral to the shoulder joint.
   a. Guide tube 13 is positioned so the axis of the pin is parallel to the plane of the table. The pin is directed from the proximal to distal direction.
4. The upper fibers of the posterior deltoid are treated by grasping the muscle tissue about 1–2 inches lateral to the shoulder joint.
   a. The needle pipe is positioned so the axis of the pin is perpendicular to the plane of the bed. The direction of the pin is toward the surface of the bed.
5. The lower fibers of the posterior deltoid can also be treated by the physician seated at the angle of the patient's ailla and trunk.
   a. The fibers of the muscle tissue is grasped between the thumb and fingers, at about 1–2 inches lateral to the shoulder joint.
   b. Guide tube 13 is positioned parallel to the plane of the table. It is placed close to the thumb, which is placed inferiorly to the other fingers. The pin points directly forward.
6. The middle deltoid can be treated at about 2 inches from the shoulder joint.
   a. The muscle tissue is grasped between the thumb and the fingers.
   b. The axis of the pin is kept parallel to the plane of the bed. The direction of the pin is directly forward.

VI. TRICEPS

A. A 50 mm pin is suggested for treating this muscle.

B. The physician is positioned at the side of the patient on the side to be treated.

C. Supine

1. For treating this muscle, the elbow can be extended or flexed.
   a. With the elbow extended, the muscle is grasped between the thumb, placed superiorly, and the fingers, placed inferiorly. To treat the lower part of the triceps, it is best to have the elbow bent to about 30–40° with the hand placed on the stomach. The muscle is pulled away from the axis of the humerus.
   b. Guide tube 13 is positioned close by the thumb so that the pin is pointing straight down towards the bed and the axis of the pin is perpendicular to the plane of the table.
2. The medial head of the triceps can be treated by abducting the shoulder to 90° with the elbow slightly bent (30–40°). The physician stands at the angle between the patient's axilla and trunk.
   a. The muscle is grasped between the thumb, placed ventrally, and the fingers, placed dorsally.
   b. The muscle is pulled away from the humerus.
   c. Guide tube 13 is positioned vertical; the pin is pointing toward the table and the axis of the pin is perpendicular (90°) to the plane of the table.

D. Prone

1. The physician is seated at the angle of the axilla and the trunk of the patient. This position is useful for treating the long head and the medial head of the triceps.
2. The patient's arm is positioned at 90° to the trunk and the elbow is bent 90°, over the edge of the table—the fingers are pointing towards the floor.
3. The muscle is grasped between the thumb, placed inferiorly, and the fingers, placed superiorly.
4. Guide tube 13 is positioned parallel to the plane of the bed, close to the thumb, with the pin pointing directly forward. The myofascial band is followed and several points can be treated along this band.

E. Side Position

1. The patient is positioned on the side opposite that which is to be treated, e.g., the patient lies on the left for treating the right triceps. The right shoulder is abducted to 90° and the elbow is bent to 90°. The palm of the hand is on the surface of the table.
2. The treating physician stands in front of the patient.
3. The muscle is grasped between the thumb, placed superiorly, and the fingers, placed inferiorly, pulling the muscle away from the long axis of the humerus.
4. Guide tube 13 is positioned vertical with the pin pointing towards the surface of the table (perpendicular to the plane of the table).

VII. INFRASPINATUS

A. A 50 mm pin is suggested for treating this muscle.

B. The physician is positioned at the side of the table.

C. Side Position

1. The patient is positioned as described for the teres major and latissimus dorsi muscle treatments.
2. Guide tube 13 is positioned 1 cm medial from the lateral edge of the scapula and parallel to the plane of the scapula. The pin is positioned to move in an inferior-to-superior direction, transverse to the plane of the muscle fibers.

D. Prone

1. The patient lies with the arm abducted to 90° and the forearm hanging over the edge of the table.
2. The needle pipe is positioned about 1 cm medial from the inferior lateral edge of the scapula and the pin is positioned to move in an inferolateral-to-superomedial direction. The pin axis is across the plane of the muscle fibers.

3. Similarly, the pin can be placed medial to the superolateral edge. The pin is positioned to move in a superolateral-to-inferomedial direction. The pin axis is across the plane of the muscle fibers.

VIII. BRACHIORADIALIS

A. A 37 mm or 50 mm pin is suggested for treating this muscle.

B. Supine

1. The treating physician sits beside the patient on the side to be treated.
2. The elbow is flexed to about 30–40° with the patient's forearm and hand resting on the stomach with palm down. The forearm is between mid-supination and mid-pronation position.
3. The muscle is grasped between the thumb, placed on the dorsum of the muscle, and the fingers, placed on the ventral aspect of the muscle.
4. Guide tube 13 is placed close to the thumb with the pin pointing in a dorsal-to-ventral direction. The axis of the pin is parallel to the plane of the table.

C. Supine

1. The elbow is slightly bent to about 20° and the forearm is supinated.
2. The upper edge of the muscle is grasped between the thumb, placed ventral, and the fingers, placed dorsally.
3. The point of stimulation is about 2 cm above the elbow crease along the lateral aspect of the lower arm in the groove made with the junction with the brachialis.
4. Guide tube 13 is held vertical to the plane of the table with the pin pointing towards the brachioradialis on the lateral aspect and towards the surface of the table.

IX. FLEXOR CARPI ULNARIS AND FLEXOR DIGITORUM PROFUNDUS

A. A 50 mm pin is suggested for treating this muscle.

B. The treating physician sits along side of the bed, and the medial border of the patient's forearm is close to the physician.

C. Supine

1. The arm is abducted at the shoulder with the elbow bent and the forearm supinated.
2. The point of stimulation is at the junction of the upper third of the forearm with the lower two-thirds of the forearm.
3. Guide tube 13 is positioned vertical with the pin pointing down towards the forearm (perpendicular to the plane of the table).

X. ADDUCTOR POLLICIS

A. The suggested pin is a 30 mm length acupuncture pin.

B. The treating physician sits along side of the bed and the patient's hand is close to the physician.

C. Supine

1. The forearm is kept between mid-pronation and mid-supination with the hand resting on its medial border.
2. The muscle is stimulated at the base of the first web space, about the junction of the bases of the first and second metacarpal bones.
3. Guide tube 13 is held vertical with the pin pointing towards the surface of the table. The plane of the pin is parallel to the plane of the palm.

D. Supine

1. Alternately, the hand can be placed on the palmar surface, with the forearm pronated.
2. The same point mentioned above can be stimulated with guide tube 13 held vertical and the pin pointing towards the surface of the table at right angles to the plane of the palm.

XI. FIRST DORSAL INTEROSSEOUS

A. The suggested pin is a 30 mm length acupuncture pin.

B. The treating physician sits along side of the bed and the patient's hand is close to the physician.

C. Supine

1. The hand is placed on the palmar surface with the forearm pronated.
2. The point of stimulus is about the midpoint of the shaft of the second metacarpal bone.
3. The muscle is pulled away from the second metacarpal bone.
4. Guide tube 13 is positioned vertical at the point with the direction of the pin towards the surface of the table, perpendicular to the plane of the palm.

XII. ABDUCTOR DIGITI MINIMI

A. The suggested pin is a 30 mm length acupuncture pin.

B. The treating physician sits along side of the bed and the patient's hand is close to the physician.

C. Supine

1. The patient's hand is placed palm down on the table.
2. The muscle is grasped between the thumb, placed near the mid-point of the muscle more dorsally, and the fingers, placed straddling the ventral aspect of the muscle.
3. Guide tube 13 is placed close to the thumb. The pin is directed perpendicularly towards the plane of the table.

XIII. ABDUCTOR POLLICIS BREVIS

A. The suggested pin is a 30 mm length acupuncture pin.

B. The treating physician sits along side of the bed and the patient's hand is close to the physician.

C. Supine

1. The patient's hand is placed palm up on the table.
2. The muscle is grasped between the fingers with the thumb medially and the other fingers laterally.
3. Guide tube 13 is placed close to the thumb. The pin is directed parallel to the plane ofthe table and the pin is positioned to move in a medial-to-lateral direction.

XIV. DORSAL INTEROSSEI

A. The suggested pin is a 30 mm length acupuncture pin.

B. The treating physician sits along side of the bed and the patient's hand is close to the physician.

C. Supine

1. The patient's hand is placed palm down on the table.
2. Guide tube 13 is placed in the web space in between the fingers at about the base of the adjacent metacarpal bones. Care must be taken to avoid the veins on the dorsum of the hand. The axis of the pin is perpendicular to the plane of the bed and the direction of the pin is toward the bed.

XV. STERNOCLEIDOMASTOID

A. The suggested pin is a 30 mm length acupuncture pin.

B. Supine

1. The treating physician stands along side near the head end of the bed, and the patient's head is close to the physician. The face is turned away to the left to treat the right side.
2. The upper portion or the lower portion of the muscle is grasped with the thumb placed at the posterior border and the fingers placed anteriorly. Guide tube 13 is positioned close to the thumb at almost horizontal to the muscle. The axis of the pin is transverse to the axis of the muscle fibers. The direction of the pin is towards the other fingers.

C. Side Position

1. The treating physician stands along side near the head end of the bed, and the patient's head is close to the physician. The uppermost side is the side to be treated. The face is turned away to the left to treat the right side.
2. The upper portion or the lower portion of the muscle is grasped with the thumb placed at the posterior border and the fingers placed anteriorly. Guide tube 13 is positioned close to the thumb almost horizontal to the muscle. The axis of the pin is transverse to the axis of the muscle fibers. The direction of the pin is towards the other fingers.

POSITIONING LOWER EXTREMITY MUSCLES FOR THE ATOIMS™ TREATMENT

Note: It is alwas important to grasp muscle tissue and identify the myofascial band before needling tool 1 is started.

XVI. GLUTEUS MAXIMUS

A. The suggested pin length is 50 or 75 mm according to the thickness of the overlying subcutaneous tissue and fat.

B. Prone

1. In this position, the treating physician stands at the side of the bed close to the side of the patient that is being treated.
2. The myofascial band that transverses along the upper third of the muscle is stimulated. This band is usually located by finding the mid-point between the tip of the coccyx and the posterior superior iliac spine. This mid-point is then joined by a line to the greater trochanter.
3. The point of stimulation is done along this line or just above this line and at the mid-point of the muscle.
4. Guide tube 13 of needling tool 1 is held vertical with the direction of the pin towards the surface of the table.

C. Side Position

1. In this position, the treating physician stands at the side of the bed, in front of the patient, close to the side of the patient that is being treated.
2. The patient is positioned on the side opposite that which is to be treated and very close to the edge of the table to be close to the physician, e.g., the patient lies on the left for treatment to the right side. The hips and knees are bent 30–60° and the ischial tuberosity is palpated.
3. Stimulation is performed above the level of the ischial tuberosity.
4. Guide tube 13 is held vertical, parallel to the plane of the body, with the pin pointing towards the surface of the table.

XVII. GLUTEUS MEDIUS

A. The suggested pin length is 37 or 50 mm according to the thickness of the overlying subcutaneous tissue and fat.

B. Side Position

1. The treating physician can stand either in front of or behind the patient.
2. The patient is positioned as for the gluteus maximus muscle (see C2 above). The patient must be very close to the edge of the table so the physician does not have to strain or lean over to reach the muscle.
3. Stimulation is performed in the outer lateral quadrant of the buttock above the level of the greater trochanter. This is a flat muscle and the muscle need not be grasped. The myofascial band or nodule is palpated and guide tube 13 is kept close to the thumb which locates the treatment point.
4. Guide tube 13 is kept vertical and the axis of the pin is parallel to the plane of the body. The direction of the pin is towards the surface of the bed.

XVIII. TENSOR FASCIA LATAE

A. The suggested pin length is 50 mm, or shorter or longer according to the thickness of the overlying subcutaneous tissue and fat.

B. Side Position

1. The treating physician may stand in front of or behind the patient.
2. The patient is positioned as for the gluteus maximus muscle (see C2 above). The treated limb is uppermost and the hip and knee are flexed 30–45'. The patient is close to the edge of the table, close to the physician.
3. If the physician stands behind the patient, the muscle is grasped about 2 inches below the anterior superior iliac spine with the thumb on the dorsal lateral surface and the fingers ventral. Guide tube 13 is positioned close to the thumb and the direction of the pin is at slight tangent to the plane of the body towards the other fingers.
4. If the physician is standing in front of the patient, the muscle is grasped with the thumb on the dorsal aspect and the fingers ventral. Guide tube 13 is positioned close to the thumb and the direction of the pin is vertically or slightly tangentially towards the other fingers.

C. Supine

1. The physician stands beside the patient close to the patient.
2. The patient lies with the hip flexed 30° and the klee in the neutral position, pointing towards the ceiling and not rotated.
3. The point of stimulation is about 2 inches distal to the anterior superior iliac spine, in the groove between the tensor fascia latae and the sartorius muscle.
4. Guide tube 13 is close to the thumb in the groove mentioned above and the tube is held vertical. The axis of the pin is perpendicular to the bed and the direction of the pin is towards the bed.

D. Seated

1. The treating physician may stand at the side of the patient or sit on the bed beside the patient. The physician may have to sit lotus-style on the table beside the patient and facing the patient to get the best angle for treatment.
2. The patient is seated at the edge of the table with the feet resting on a stool so that the knees are higher than the hips. The knees are in the neutral position, pointing towards the ceiling and not rotated outward.
3. The point of stimulation is about 2 inches from the anterior superior iliac spine in the groove mentioned above.
4. Guide tube 13 is held vertical with the pin directed towards the table.

XIX. RECTUS FEMORIS AND SARTORIUS

A. The suggested pin length is 50 mm, or shorter or longer according to the thickness of the overlying subcutaneous tissue and fat.

B. Supine

1. The physician stands close beside the patient.
2. The patient lies with the hip and knee flexed to about 60° with the knee in neutral position and not rotated.
3. The muscle is grasped at about the upper third of the thigh with the thumb placed medially and the fingers placed laterally or vice versa.

4. Guide tube 13 is placed close to the thumb, almost parallel to the plane of the table. The pin is pointing in a medial-to-lateral direction, towards the fingers, or a lateral-to-medial direction, towards the fingers.

C. Side Position

1. The treating physician stands behind the patient.
2. The patient lies on the side opposite that which is to be treated. The side to be treated is uppermost e.g., the right is uppermost if this is the side to be treated. The right hip and knee are flexed 45'.
3. The muscle is grasped between the thumb on the dorsolateral aspect and the fingers on the ventral aspect.
4. Guide tube 13 is placed close to the thumb with the pin pointing in a posterior-to-anterior direction, towards the other fingers at a tangent to the body.

XX. VASTUS MEDIALIS

A. The suggested pin length is 50 mm, or shorter or longer according to the thickness of the overlying subcutaneous tissue and fat.

B. Supine

1. The physician stands beside the patient close to the patient.
2. The muscle is grasped between the thumb superiorly and the fingers inferiorly. The muscle is pulled away from the bone. The hips and knees are slightly bent.
3. Guide tube 13 is positioned close to the thumb with the direction of the pin being parallel to the plane of the axis of the thigh and towards the surface of the table.

C. Side Position

1. The treating physician stands in front of the patient.
2. The patient lies on the side opposite that which is to be treated. The patient lies on the left side to have the right side treated. The right hip is flexed 60' or so and slightly abducted.
3. Guide tube 13 is positioned almost parallel to the plane of the thigh. The pin is pointing in a distal-to-proximal direction and the axis of the pin is transverse to the axis of the muscle fibers.

XXI VASTUS LATERALIS

A. The suggested pin length is 50 mm, or shorter or longer according to the thickness of the overlying subcutaneous tissue and fat.

B. Supine

1. The treating physician stands beside the patient.
2. Stimulation point is at the lateral aspect of the thigh. The muscle is grasped between the thumb superiorly and the fingers inferiorly at about mid-third of the thigh or lower one-third of the thigh.
3. Guide tube 13 is positioned close to the thumb and held vertical, parallel to the plane of the thigh. The pin is directed in a ventral-to-dorsal direction, vertical to the plane of the table.

XXII. SEMITENDINOSUS

A. The suggested pin length is 50 mm, or shorter or longer according to the thickness of the overlying subcutaneous tissue and fat.

B. Side Position

1. The treating physician stands in front of the patient.
2. The patient lies on the side opposite that which is to be treated, i.e., the patient lies on the left to have the right side treated.
   a. The muscle is grasped at its proximal part, just below the ischial tuberosity with the thumb placed dorsally and the other fingers placed ventrally.
   b. Guide tube 13 is positioned vertical adjacent to the thumb with the direction towards the fingers and the surface of the table.
3. Alternatively, the patient can lie on the side to be treated, e.g., the patient lies on the right to have the right side treated. The right hip and knees are flexed to about 30°.
   a. The muscle is gasped between the thumb ventrally and the fingers dorsally.
   b. Guide tube 13 is placed vertically close to the thumb with the direction of the pin towards the surface of the table towards the other fingers.

XXIII BICEPS FEMORIS—Long Head (See above description for SEMITENDINOSUS).

XXIV. BICEPS FEMORIS—Short Head

A. The suggested pin length is 37 mm, or shorter or longer according to the thickness of the overlying subcutaneous tissue and fat.

B. Prone

1. The treating physician stands beside the patient close to the side that is being treated.
2. The treatment point is at medial to the long head of the biceps femoris in the lower one third of the thigh The thumb palpates for the myofascial band and guide tube 13 is positioned vertically close to the thumb. The pin is directed towards the table vertical to the plane of the table.

XXV. LATERAL AND MEDIAL GASTROCNEMIUS

A. The suggested pin length is 50 mm, or shorter or longer according to the thickness of the overlying subcutaneous tissue and fat.

B. Side Position

1. The physician stands at the side of the table close to the patient.
2. The patient can be positioned on the left side and the legs are slightly spread apart. The left knee is kept bent to 60° or so and the right knee straight to treat the right lateral gastrocnemius muscle and the left medial gastrocnemius muscle, respectively.
3. The right lateral gastrocnemius to be treated is uppermost and is grasped between the thumb superiorly and other fingers ventrally. Guide tube 13 is placed close to the thumb which locates the myofascial band. The needle is directed towards the table and the axis is at a tangent to the shaft of the tibial bone.
4. The medial gastrocnemius on the right leg is treated in the same fashion.

C. Supine

1. The physician stands at the side of the table, close to the patient.
2. The lateral gastrocnemius is treated by grasping the muscle between the thumb placed laterally and the fingers placed medially.
3. Guide tube 13 is placed close to the thumb with the pin in a lateral-to-medial direction, parallel to the plane of the table.
4. The medial gastrocnemius of the opposite leg is treated in the same manner.

XXVI. ADDUCTOR MAGNUS

A. The suggested pin length is 50 mm, or shorter or longer according to the thickness of the overlying subcutaneous tissue and fat.

B. Supine

1. The treating physician stands beside the patient close to the side that is being treated. The patient's hip and knee are completely flexed so that the knee almost touches the table with the hip in external rotation.

2. The muscle is grasped with the thumb on the ventromedial aspect of the thigh and the fingers on the dorsomedial aspect.

3. Guide tube 13 is placed close to the thumb. The pin is directed down towards the table.

C. Prone

1. Grasp the muscle on the inner most aspect of the thigh, with the thumb on the dorsal aspect and the other fingers on the ventral aspect. The physician must stand close to the patient near the side to be treated.

2. Guide tube 13 is placed vertically, close to the thumb with the direction of the pin towards the table, in a plane parallel to the treated thigh.

XXVII. TIBIALIS ANTERIOR

A. The suggested pin length is 37 mm, or shorter or longer according to the thickness of the overlying subcutaneous tissue and fat.

B. Supine

1. The physician stands beside the table and close to the patient. The knee and hip is flexed about 45'.

2. The muscle is grasped with the thumb about 1 cm away from the edge of the tibial bone and the fingers straddling the muscle at about the junction of the upper and middle third of the leg.

3. Guide tube 13 is placed close to the thumb. The pin is directed down towards the table and the other fingers.

XXVIII. ABDUCTOR HALLUCIS MUSCLE

A. The suggested pin is a 30 mm acupuncture pin.

B. Supine

1. The physician stands beside the table and close to the patient. The foot lies on its lateral border.

2. Guide tube 13 is positioned at the motor point of the muscle close to the thumb which is near the navicular bone. The direction of the pin is towards the lateral border of the foot.

XXIX. ABDUCTOR DIGITI QUINTI

A. The suggested pin is a 30 mm acupuncture pin.

B. Supine

1. The physician stands beside the table and close to the patient. The foot is in neutral position.

2. Needling tool 1 is positioned at the motor point of the muscle close to the thumb which is in front of or behind the base of the fifth metatarsal bone. The plane of guide tube 13 is parallel to the shaft of the tibia and the pin is directed distally.

XXX. INTEROSSEI

A. The suggested pin is a 30 mm acupuncture pin.

B. Supine

1. The physician stands beside the table and close to the patient. The foot is in neutral position.

2. Needling tool 1 is positioned with its long axis parallel to the shaft of the tibia bone and between bases of the metatarsal bones. The direction of the pin is towards the distal direction.

3. The hip and knee can be flexed so that the sole ofthe foot is on the bed. Needling tool 1 is positioned vertically and between the bases of the metatarsal bones. The direction of the pin is directly down towards the bed.

XXI. PARASPINAL MUSCLES

A. 37 mm pins are suitable for treatment from the C5 down to the T12 levels. From the L1 through S1 levels, a 50 mm pin may be needed, depending on the thickness of the subcutaneous tissues overlying the spine.

B. Prone

1. The treating physician stands beside the patient close to the side that is being treated.

2. The point of stimulation is about 1 cm away from the spinous process.

3. The middle finger must be placed on the spinous process to identify this structure before needling tool 1 is started.

The present invention has been described in terms of preferred and exemplary embodiments thereof Numerous other embodiments and variations within the scope and spirit of the appended claims will occur to persons skilled in the art, from a review of this disclosure.

We claim:

1. An automatic needling device for facilitating intramuscular stimulation pain relief therapy, comprising:

an elongated guide tube having a skin contact member at a distal end of said tube;

a plunger rod reciprocable within said guide tube, said plunger rod having a proximal end protruding from a proximal end of said guide tube and a distal end retained within said tube and providing a needle holder;

a needle securable at its proximal end to said needle holder and reciprocable with said plunger rod for movement into and out of said guide tube through said skin contact member;

a motorized shuttle mechanism attached to said protruding proximal end of said plunger rod for reciprocating said plunger rod within said guide tube, whereby a needle secured to said needle holder is caused to reciprocate in and out of said guide tube through said skin contact member; and electronic circuitry for controlling the motorized shuttle mechanism to advance the needle from a non-protruding position within said guide tube out of said guide tube to a predetermined penetration depth, reciprocate the needle back and forth through a predetermined stroke length a predetermined number of times, and retract the needle back to a non-protruding position within said guide tube.

2. An automatic needling device according to claim 1, wherein said electronic circuitry controls the motorized shuttle mechanism to drive the needle into the patient's flesh at a velocity of no more than 0.6 m/sec.

3. An automatic needling device according to claim 1, wherein said electronic circuitry controls the motorized shuttle mechanism to reciprocate the needle at a rate of between one and three cycles per second.

4. An automatic needling device according to claim 3, wherein said electronic control circuit controls the motorized shuttle mechanism to reciprocate the needle at a rate of about two cycles per second.

5. An automatic needling device according to claim 1, wherein said motorized shuttle mechanism comprises a rotary motor and a mechanical linkage for converting the rotary motion of said rotary motor to reciprocable linear motion of said plunger rod.

6. An automatic needling device according to claim 5, wherein said rotary motor is a stepper motor.

7. An automatic needling device according to claim 5, wherein said mechanical linkage comprises a gear wheel engaged with a flat gear.

8. An automatic needling device according to claim 1, wherein said guide tube, plunger rod and needle are incorporated into a hand-held tool.

9. An automatic needling method for facilitating intramuscular stimulation pain relief therapy, comprising:

pre-positioning a skin contact member of an automatic needling device at a chosen site on a patient's skin with a needle of the device in a non-protruded position with respect to said skin contact member; and controlling said automatic needling device to automatically advance said needle thereof from said non-protruded position to a predetermined penetration depth within the patient's flesh and reciprocate the needle back and forth through a predetermined stroke length a predetermined number of times, and retracting the needle from the patient's flesh.

10. An automatic needling method according to claim 9, further comprising localizing as a twitch point a tender point on a myofascial band of muscle of the patient, and wherein said skin contact member of the automatic needling device is pre-positioned on the skin over said twitch point.

11. An automatic needling method according to claim 10, wherein said automatic needling device is controlled to reciprocate the needle back and forth three times and then to retract the needle from the patient's flesh.

12. An automatic needling method according to claim 9, wherein said automatic needling device is controlled to drive the needle into the patient's flesh at a velocity of no more than 0.6 m/sec.

13. An automatic needling method according to claim 9, wherein said automatic needling device is controlled to reciprocate the needle at a rate of between one and three cycles per second.

14. An automatic needling method according to claim 13, wherein said automatic needling device is controlled to reciprocate the needle at a rate of about two cycles per second.

15. An automatic needling method according to claim 9, wherein said retraction of the needle from the patient's flesh comprises automatic retraction of the needle to said non-protruded position by said automatic needling device.

16. An automatic needling device according to claim 15, wherein said electronic circuitry controls the motorized shuttle mechanism to reciprocate the needle back and forth three times and then to retract the needle back to a non-protruding position within said guide tube.

17. An automatic needling method according to claim 15, wherein said automatic retraction is performed while the skin contact member is maintained at said chosen site.

18. A needling device for facilitating intramuscular stimulation pain relief therapy, comprising:

an elongated guide tube having a skin contact member forming a constricted orifice at a distal end of said tube;

a plunger rod reciprocable within said guide tube, said plunger rod having a proximal end protruding from a proximal end of said guide tube and a distal end retained within said tube and providing a needle holder;

a needle securable at its proximal end to said needle holder and reciprocable with said plunger rod for movement from a non-protruding position within said guide tube out of said guide tube through said constricted orifice of the skin contact member, said constricted orifice being sized large enough to allow substantially free passage of the needle back and forth therein but small enough to serve as a needle guide preventing significant flexing of the needle at the point of entry into a skin surface contacted by said skin contact member.

19. A needling device according to claim 18, wherein said constricted orifice has an inner diameter which exceeds a diameter of said needle by less than 0.50 mm.

20. A needling device according to claim 19, wherein said orifice has an inner diameter of 0.75 mm and said needle has a diameter in the range of 0.26 mm–0.46 mm.

21. Aneedling device according to claim 18, wherein an internal diameter of said guide tube tapers to said constricted orifice in a funnel-like manner.

22. A needling device according to claim 18, further comprising:

a motorized shuttle mechanism attached to said plunger rod for reciprocating said plunger rod within said guide tube, whereby a needle secured to said needle holder is caused to reciprocate in and out of said guide tube through said skin contact member; and electronic circuitry for controlling the motorized shuttle mechanism to advance the needle out of said guide tube to a predetermined penetration depth, reciprocate the needle back and forth through a predetermined stroke length a predetermined number of times, and retract the needle into said guide tube.

* * * * *

UNITED STATES PATENT AND TRADEMARK OFFICE

CERTIFICATE OF CORRECTION

PATENT NO. : 5,968,063
DATED : October 19, 1999
INVENTOR(S) : Jennifer CHU

It is certified that error appears in the above-identified patent and that said Letters Patent is hereby corrected as shown below:

In Claim 4, column 20, line 50, delete "circuit" and insert --circuitry--.

In Claim 21, column 22, line 26, delete "Aneedling" and insert --A needling--.

Signed and Sealed this

First Day of August, 2000

Attest:

Q. TODD DICKINSON

*Attesting Officer* *Director of Patents and Trademarks*